United States Patent
Munir et al.

(10) Patent No.: US 12,172,577 B2
(45) Date of Patent: Dec. 24, 2024

(54) SYSTEM AND METHOD OF CAPTURING PHYSIOLOGICAL ANOMALIES UTILIZING A VEHICLE SEAT

(71) Applicant: Robert Bosch GmbH, Stuttgart (DE)

(72) Inventors: Sirajum Munir, Pittsburgh, PA (US); Samarjit Das, Wexford, PA (US)

(73) Assignee: Robert Bosch GmbH (DE)

( * ) Notice: Subject to any disclaimer, the term of this patent is extended or adjusted under 35 U.S.C. 154(b) by 167 days.

(21) Appl. No.: 17/853,354

(22) Filed: Jun. 29, 2022

(65) Prior Publication Data
US 2024/0001842 A1 Jan. 4, 2024

(51) Int. Cl.
*B60Q 9/00* (2006.01)
*A61B 5/00* (2006.01)
*B60N 2/00* (2006.01)
*B60N 2/26* (2006.01)
*G10L 25/24* (2013.01)
*G10L 25/51* (2013.01)

(52) U.S. Cl.
CPC .............. *B60Q 9/00* (2013.01); *A61B 5/6893* (2013.01); *A61B 5/7267* (2013.01); *B60N 2/002* (2013.01); *B60N 2/26* (2013.01); *G10L 25/24* (2013.01); *G10L 25/51* (2013.01); *A61B 2562/0204* (2013.01); *A61B 2562/046* (2013.01)

(58) Field of Classification Search
None
See application file for complete search history.

(56) References Cited

U.S. PATENT DOCUMENTS

| | | | | |
|---|---|---|---|---|
| 8,706,204 | B2* | 4/2014 | Seo | A61B 5/02 600/509 |
| 11,518,411 | B2* | 12/2022 | Hanawa | G05D 1/0011 |
| 11,524,691 | B2* | 12/2022 | Gallagher | A61B 5/18 |
| 2011/0137209 | A1* | 6/2011 | Lahiji | H04R 1/406 600/586 |

(Continued)

FOREIGN PATENT DOCUMENTS

DE 102016003312 A1 10/2016

OTHER PUBLICATIONS

English language translation of DE102016003312A1, Albrecht et al., Oct. 6, 2016. (Year: 2016).*

(Continued)

*Primary Examiner* — Paul W Huber
(74) *Attorney, Agent, or Firm* — Dickinson Wright PLLC (57) ABSTRACT

A vehicle system that includes a vehicle seat, wherein the vehicle seat includes a seat-back portion, a seat-bottom portion, a head rest portion, wherein the vehicle seat includes one or more acoustic sensors configured to retrieve an acoustic signal associated with a passenger seat, and a processor in communication with at least the one or more acoustic sensors, wherein the processor is programmed to identify an anomaly associated with the passenger utilizing the acoustic signal, wherein the anomaly is identified via pre-processing the acoustic signal and extracting one or more features associated with the acoustic signal in response to the pre-preprocessing and utilizing a classifier to classify one or more features associated with the acoustic signal as either a normal condition or the anomaly, and output a notification associated with the anomaly in response to identifying the anomaly.

18 Claims, 6 Drawing Sheets

(56) References Cited

U.S. PATENT DOCUMENTS

| | | | |
|---|---|---|---|
| 2015/0201272 A1* | 7/2015 | Wong | A61B 7/04 |
| | | | 381/67 |
| 2019/0225232 A1* | 7/2019 | Blau | G05D 1/0088 |
| 2022/0330836 A1 | 10/2022 | Schmalenberg et al. | |
| 2022/0330848 A1* | 10/2022 | Ferraris | H04R 1/1083 |
| 2022/0338814 A1* | 10/2022 | Babu | A61B 5/7214 |

OTHER PUBLICATIONS

Drugman et al., "Voice activity detection: Merging source and filter-based information", IEEE Signal Processing Letters, vol. 23, issue 2, 2017, 5 pages.

Brandstein et al., "A practical methodology for speech source localization with microphone arrays." Computer Speech & Language 11.2 (1997), 36 pages.

Aytar et al., "Soundnet: Learning sound representations from unlabeled video." Advances in neural information processing systems. 2016, 9 pages.

Dai et al., "Very deep convolutional neural networks for raw waveforms", IEEE International Conference on Acoustics, Speech and Signal Processing (ICASSP), 2017, 5 pages.

* cited by examiner

SYSTEM AND METHOD OF CAPTURING PHYSIOLOGICAL ANOMALIES UTILIZING A VEHICLE SEAT

TECHNICAL FIELD

The present disclosure relates to seats, such as those in a vehicle, which may utilize a microphone.

BACKGROUND

People use cars to commute to a variety of places. While someone is on a car seat and the car is moving, the person is usually static, and this provides a great opportunity to sense physiological parameters of the individual. We propose to leverage this opportunity to sense a wide range of cardiovascular and respiratory issues, including but not limited to heart murmur, heart arrythmia, coronary artery disease, coughing, sneezing, wheezing, shortness of breath, and asthma. In order to do this, we propose to instrument a car seat with one or more microphone or acoustic sensors. The proposed work is not limited to instrumenting the driver's seat only. It can be instrumented to each seat of a car. Also, it can be instrumented in an infant/toddler car seat. It can also be instrumented to bus, truck, and airplane seats as well. In addition, the chairs in other places including houses, commercial places, hospitals, airports, stadiums, and convention centers can be instrumented and can be used for the proposed work.

SUMMARY

A first embodiment discloses a vehicle system that includes a vehicle seat, wherein the vehicle seat includes a seat-back portion, a seat-bottom portion, a head rest portion, wherein the vehicle seat includes one or more acoustic sensors configured to retrieve an acoustic signal associated with a passenger seat, and a processor in communication with at least the one or more acoustic sensors, wherein the processor is programmed to identify an anomaly associated with the passenger utilizing the acoustic signal, wherein the anomaly is identified via pre-processing the acoustic signal and extracting one or more features associated with the acoustic signal in response to the pre-preprocessing and utilizing a classifier to classify one or more features associated with the acoustic signal as either a normal condition or the anomaly, and output a notification associated with the anomaly in response to identifying the anomaly.

A second embodiment discloses a vehicle system that includes a vehicle seat, wherein the vehicle seat includes a seat-back portion, a seat-bottom portion, wherein the vehicle seat includes one or more acoustic sensors configured to retrieve an acoustic signal associated with a passenger seat, and a processor in communication with at least the one or more acoustic sensors, wherein the processor is programmed to classify the acoustic signal as an anomaly or normal condition, wherein the classifying is accomplished pre-processing the acoustic signal and extracting one or more features associated with the acoustic signal in response to the pre-preprocessing and utilizing a classifier to classify one or more features associated with the acoustic signal as the normal condition or the anomaly, and output a notification associated with the anomaly in response to identifying the anomaly.

A third embodiment discloses a system that includes a processor in communication with at least one or more acoustic sensors located in a seat, wherein the processor is programmed to identify an anomaly associated with the passenger utilizing the acoustic signal, wherein the anomaly is identified via pre-processing the acoustic signal and extracting one or more features associated with the acoustic signal in response to the pre-preprocessing and utilizing one or more features associated with the acoustic signal as the anomaly, and output a notification associated with the anomaly in response to identifying the anomaly.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

People may use vehicles for various scenarios, such as for commuting to work and to go to many other places on a regular basis. While someone is on a car seat, the body movement is constrained while the car is in motion. We leverage this constrained setup to opportunistically sense the physiological parameters to detect health anomalies. In particular, within the scope of this invention, we instrument car seats with microphones or acoustic sensors that listens to heart sounds (audible and infrasound) and other physiologically meaningful sounds emanating from the body to detect a wide range of health issues, including but not limited to heart murmur, heart arrhythmia, coronary artery disease, and other cardiovascular diseases. It can also be useful for detecting coughing, sneezing, wheezing, shortness of breath, asthma, and other respiratory diseases.

Figure 1:
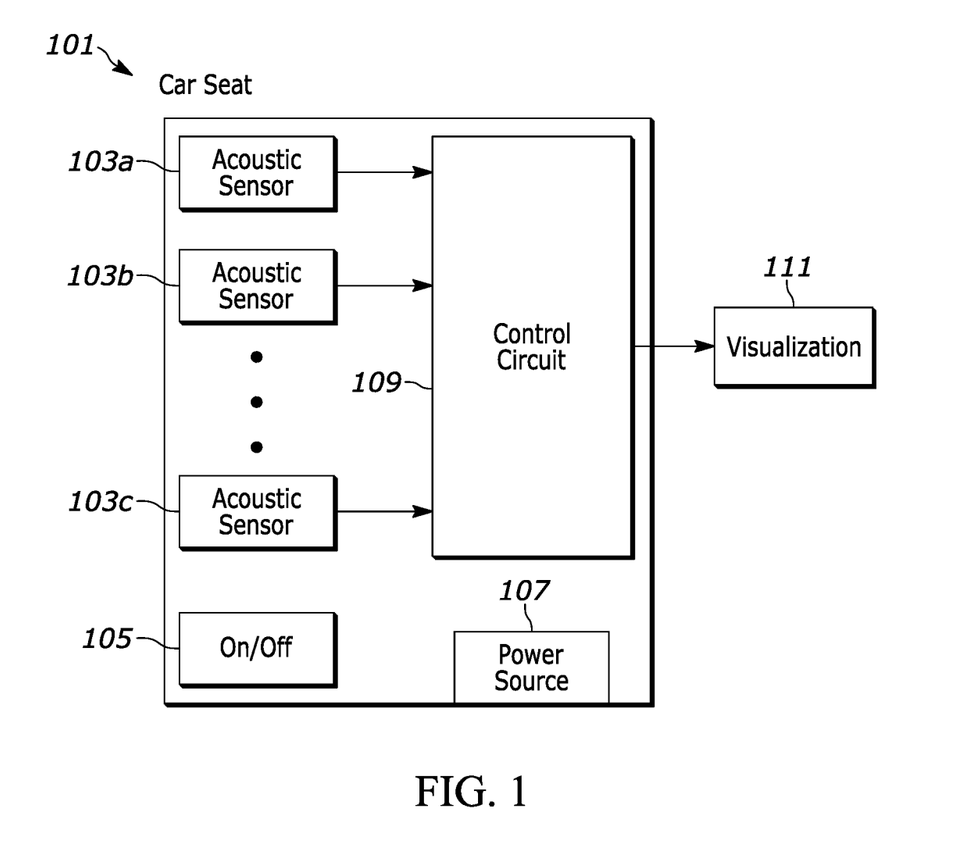
FIG. 1 discloses an embodiment of a schematic diagram as related to a vehicle seat that includes acoustic sensors.

FIG. 1 discloses a schematic. The vehicle seat 101 may include various components to help listen for physiological anomalies. The vehicle seat 101 may be any type of seat, such as an infant car seat, toddler car seat, bus seat, train seat, airplane seat, motorcycle seat, etc. For example, the vehicle seat 101 may include one or more acoustic sensors 103a, 103b, 103c. As explained further below, the acoustic sensors may be arranged in any manner in the vehicle seat. The acoustic sensors 103 may be arranged under a perforation(s) of the seat. In one embodiment, the acoustic sensors 103 may be in a seat-back portion of the vehicle seat 101, however, any area of the vehicle seat may suffice. The acoustic sensors 103a, 103b, 103c, may be any type of sensor that can pick up any sound or acoustic signal, such as a microphone, sonar, Thickness-Shear Mode resonator, surface acoustic wave (SAW) sensor, Shear-Horizontal Acoustic Plate Mode (SH APM) sensor, Flexural Plate Wave (FPW) sensor, etc.

Conversion of acoustic energy to electrical energy and electrical energy to acoustic energy is known in the art. Conversion of digital signals to analog signals and conversion of analog signals to digital signals is also known. Processing digital representations of energy and analog representations of energy either in hardware or by software directed components is also well known.

Separately, there may be an on/off 105 button located in the vehicle system. The one/off 105 switch may be utilized to turn off power to the vehicle seat or at least the acoustic sensors. If a switch is ON, it has a value of 1 or zero (0) and may activate power to its components. If it is OFF it may have no value, so it may be represented with an "0." The same may be true for the state of the switch being ON or OFF. When you are looking at a schematic and reading the values for each switch position, you are counting from left to right. Additionally, a power source 107 may be located in the vehicle seat or connecting to the vehicle seat. The power source 107 may provide power to the one or more acoustic sensors 103, additionally to other components. The power source 107 may be connected to a vehicle alternator, battery, or any other energy source (e.g. solar, etc.).

The control circuit 109 may include a controller or a processor. The control circuit may include both volatile and non-volatile storage. Non-volatile storage may be included one or more persistent data storage devices such as a hard drive, optical drive, tape drive, non-volatile solid-state device, cloud storage or any other device capable of persistently storing information. The processor may include one or more devices selected from high-performance computing (HPC) systems including high-performance cores, microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on computer-executable instructions residing in memory. Memory may include a single memory device or a number of memory devices including, but not limited to, random access memory (RAM), volatile memory, non-volatile memory, static random access memory (SRAM), dynamic random access memory (DRAM), flash memory, cache memory, or any other device capable of storing information.

Processor may be configured to read into memory and execute computer-executable instructions residing in non-volatile storage and embodying one or more algorithms and/or methodologies of one or more embodiments. Non-volatile storage may include one or more operating systems and applications. Non-volatile storage may store compiled and/or interpreted from computer programs created using a variety of programming languages and/or technologies, including, without limitation, and either alone or in combination, Java, C, C++, C#, Objective C, Fortran, Pascal, Java Script, Python, Perl, and PL/SQL.

Upon execution by processor, the computer-executable instructions of non-volatile storage may cause control system to implement one or more of the algorithms and/or methodologies as disclosed herein. Non-volatile storage may also include machine learning (ML) data (including data parameters) supporting the functions, features, and processes of the one or more embodiments described herein.

The program code embodying the algorithms and/or methodologies described herein is capable of being individually or collectively distributed as a program product in a variety of different forms. The program code may be distributed using a computer readable storage medium having computer readable program instructions thereon for causing a processor to carry out aspects of one or more embodiments. Computer readable storage media, which is inherently non-transitory, may include volatile and non-volatile, and removable and non-removable tangible media implemented in any method or technology for storage of information, such as computer-readable instructions, data structures, program modules, or other data. Computer readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer. Computer readable program instructions may be downloaded to a computer, another type of programmable data processing apparatus, or another device from a computer readable storage medium or to an external computer or external storage device via a network.

Computer readable program instructions stored in a computer readable medium may be used to direct a computer, other types of programmable data processing apparatus, or other devices to function in a particular manner, such that the instructions stored in the computer readable medium produce an article of manufacture including instructions that implement the functions, acts, and/or operations specified in the flowcharts or diagrams. In certain alternative embodiments, the functions, acts, and/or operations specified in the flowcharts and diagrams may be re-ordered, processed serially, and/or processed concurrently consistent with one or more embodiments. Moreover, any of the flowcharts and/or diagrams may include more or fewer nodes or blocks than those illustrated consistent with one or more embodiments.

The processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

The visualization output 111 may include a display. The display may include any vehicle display, such as a multimedia display. The system may also include a humanmachine interface (HMI) display. The HMI display may include any type of display within a vehicle cabin. Such HMI display may include a dashboard display, navigation display, multimedia display, heads-up display, thin-film transistor liquid-crystal display (TFT LCD), etc. The HMI display may also be connected to speakers to output sound related to commands or the user interface of the vehicle. The HMI display may be utilized to output various commands or information to occupants (e.g. driver or passengers) within the vehicle. For example, in an automatic braking scenario, the HMI display may display a message that the vehicle is prepared to brake and provide feedback to the user regarding the same. The HMI display may utilize any type of monitor or display utilized to display relevant information to the occupants. In addition to providing visual indications, the display may also be configured to receive user input via a touch-screen, user interface buttons, etc. The display may be configured to receive user commands indicative of various vehicle controls such as audio-visual controls, autonomous vehicle system controls, certain vehicle features, cabin temperature control, etc. The controller may receive such user input and in turn command a relevant vehicle system of the component to perform in accordance with the user input.

Figure 2A:
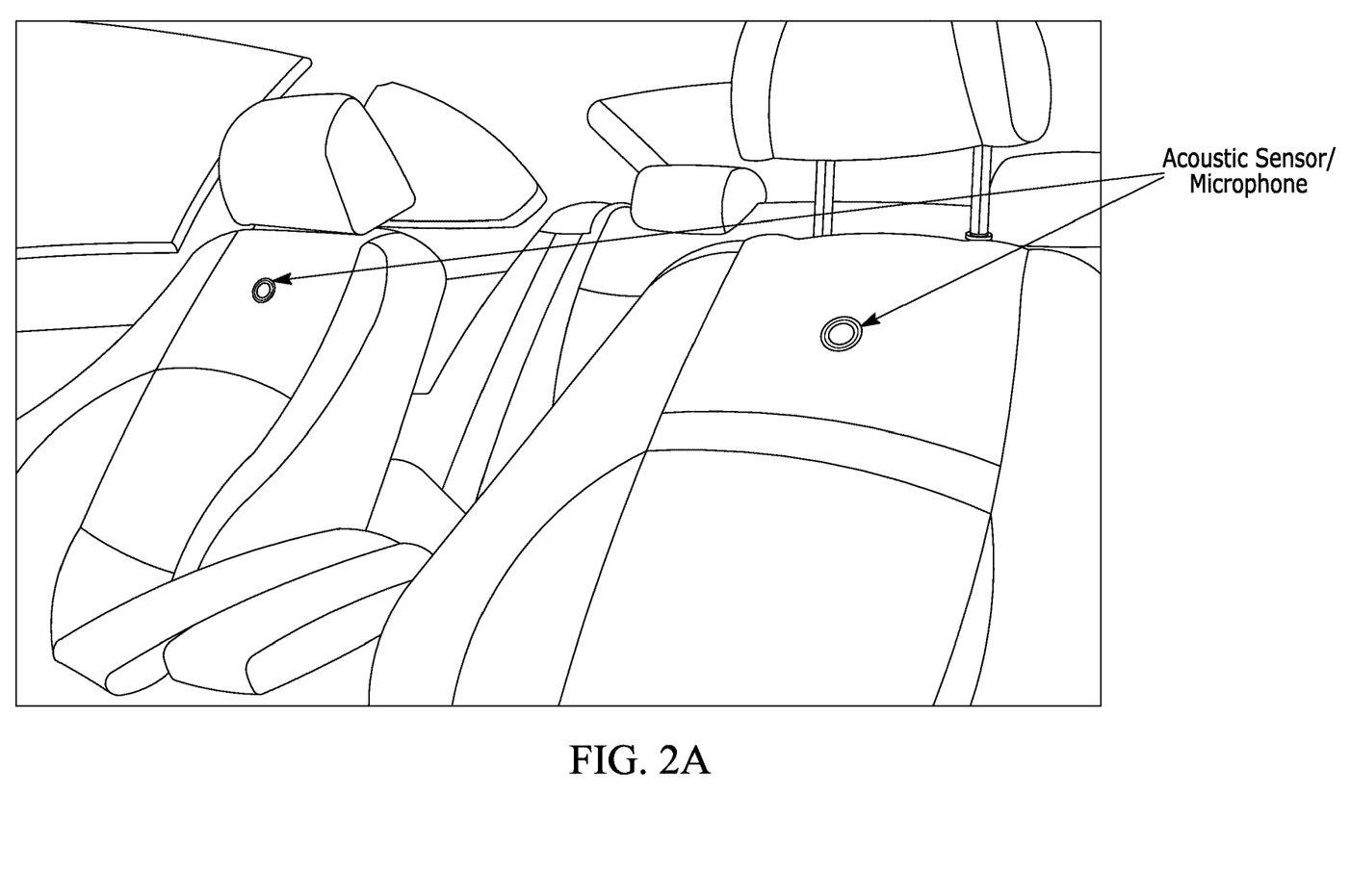
FIG. 2A discloses a first embodiment of a vehicle seat including one unit.
Figure 2B:
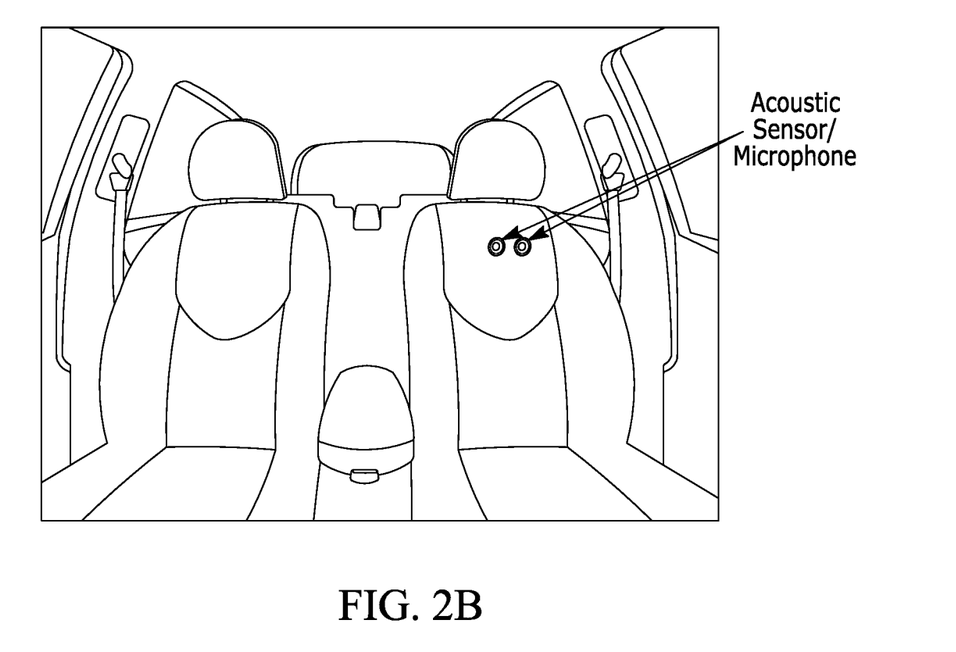
FIG. 2B disclose a second embodiment of a vehicle seat including two units.
Figure 2C:
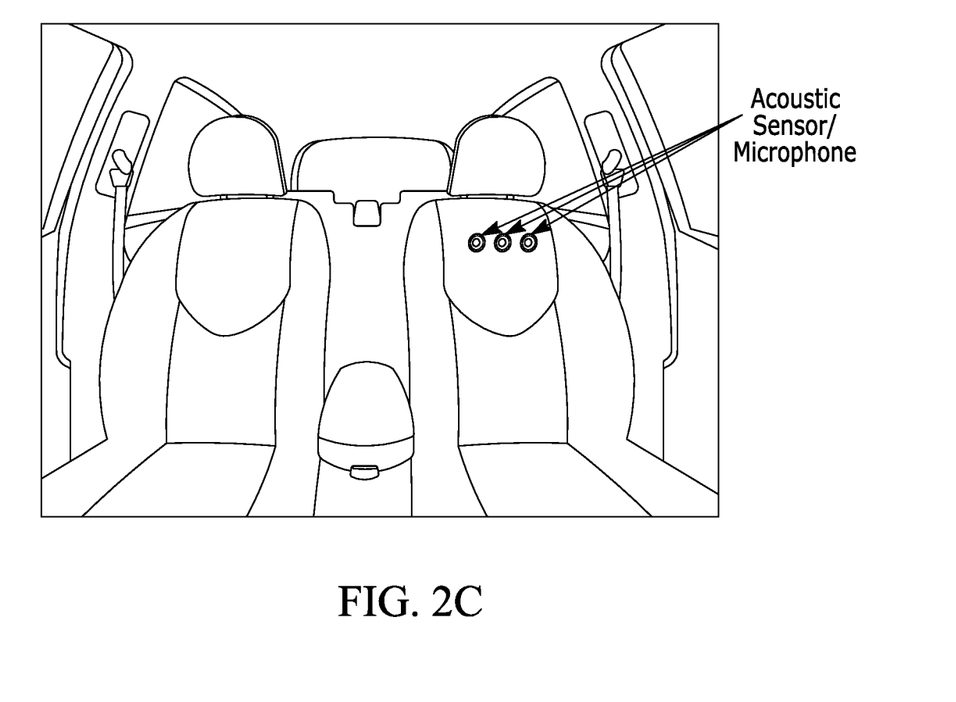
FIG. 2C discloses a third embodiment of a vehicle seat including three units.
Figure 2D:
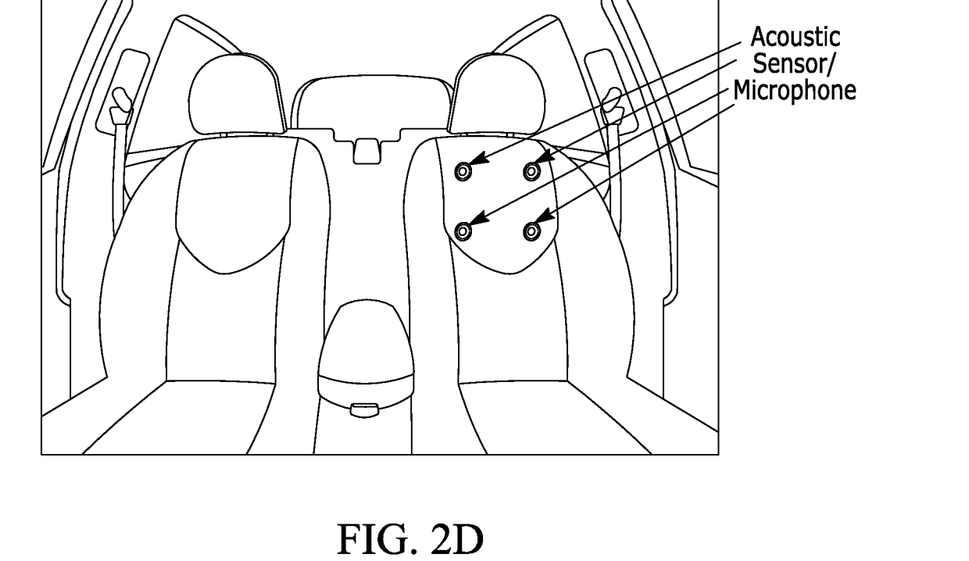
FIG. 2D disclose a fourth embodiment with a rectangular array of four units.
Figure 2E:
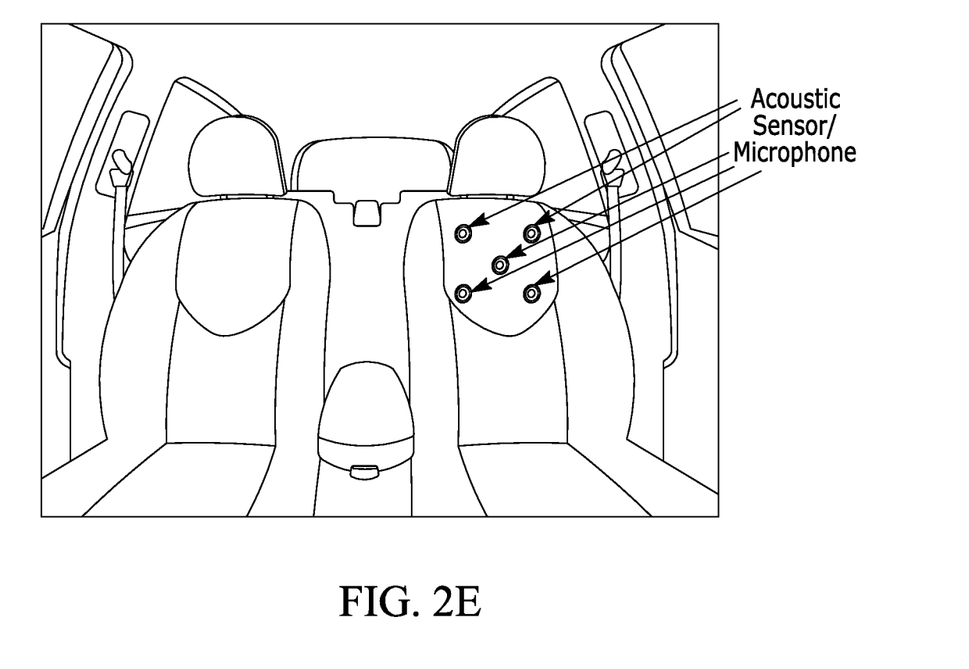
FIG. 2E discloses a fifth embodiment with a rectangular array of five units.
Figure 2F:
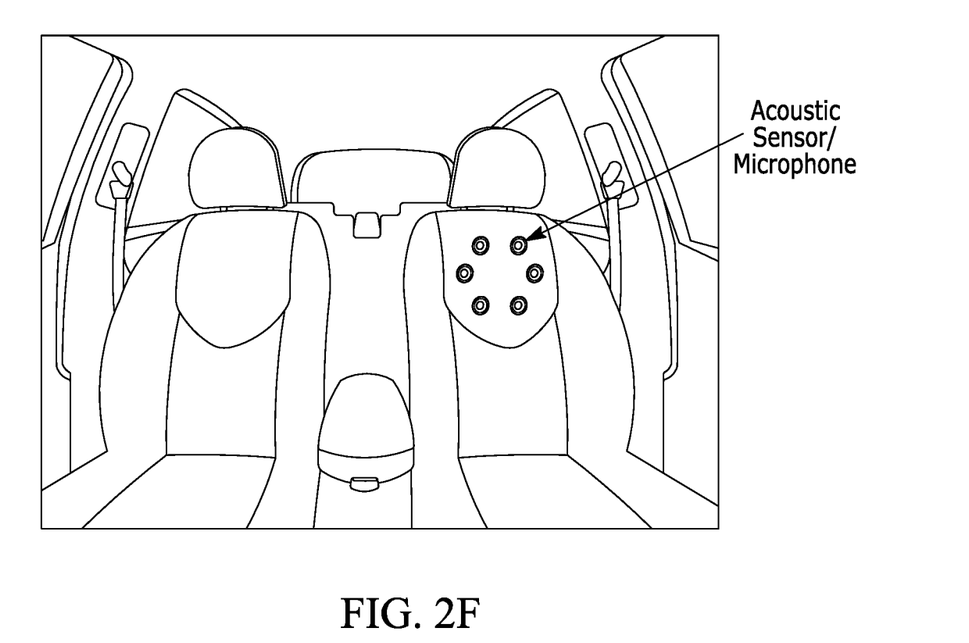
FIG. 2F discloses a sixth embodiment with a circular array with six units.
Figure 2G:
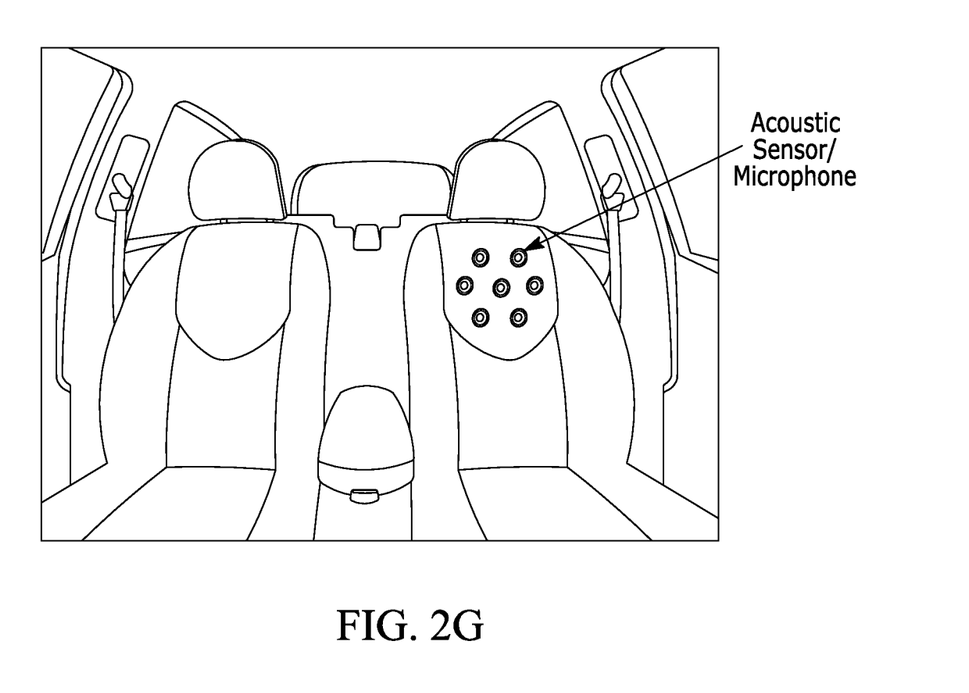
FIG. 2G discloses a seventh embodiment with a circular array with seven units.

FIG. 2A discloses a first embodiment of a vehicle seat including one unit. FIG. 2B disclose a second embodiment of a vehicle seat including two units. In such an embodiment, the acoustic sensors or microphones may be located in the seat-back portion of the vehicle seat. In the embodiment of FIG. 2A, only one acoustic sensor may be utilized. In FIG. 2B, two acoustic sensors may be utilized. The sensors may be in a single seat (e.g., driver seat or passenger seat), or in all seats, or any combination thereto. In FIG. 2B, the two sensors may be lined up in a linear array with two units. FIG. 2C discloses a third embodiment of a vehicle seat including three units. FIG. 2D disclose a fourth embodiment with a rectangular array of four units. FIG. 2E discloses a fifth embodiment with a rectangular array of five units. Such an array may be a rectangular array. The additional sensors in the rectangular array may be able to detect acoustic waves emitted form a user. In one embodiment, the acoustic waves may be penetrated through perforations of the seat. FIG. 2F discloses a sixth embodiment with a circular array with six units. FIG. 2G discloses a seventh embodiment with a circular array with seven units. Such an array may be a circular array. The additional sensors in a circular array may be able to detect acoustic waves emitted form a user. In one embodiment, the acoustic waves may be penetrated through perforations of the seat.

Figure 3:
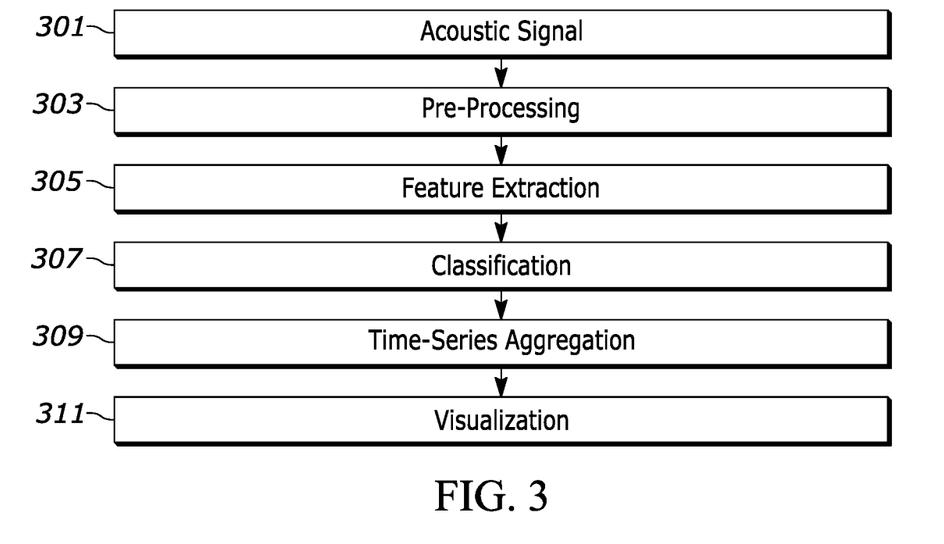
FIG. 3 discloses a flowchart of a computing pipeline for detecting physiological anomaly.

FIG. 3 discloses a flowchart of a computing pipeline for detecting physiological anomaly. In such an embodiment, each physiological anomaly may be represented as a class. The system may have a class for normal health conditions as well. The system may capture time-frequency domain acoustic features (e.g., Mel-spectorgram) from each window of a sensing period and then classify the window utilizing a classifier, e.g., an SVM, random forest, or a multilayer perceptron. After the classification is performed, the classification result may show whether the person has a normal health condition or has a physiological anomaly. The classification result may also describe the type of anomaly, e.g., heart arrhythmia based on the class with the highest confidence score. At step 301, the system may collect an acoustic signal. The acoustic signal may come from a one or more acoustic sensors. The acoustic sensors may all be the same type of sensor or may be a mix of various types of sensors. The acoustic sensor may be utilized to collect information related to the user to identify any strange behavior or patterns. The sensors may listen to audio at a specific sampling rate. At step 303, the system may retrieve the acoustic signals for pre-processing at a circuit and/or microphones. At step 305, the pre-processed acoustic signal may be fed to a controller or another circuit for feature extraction. The feature extraction may be utilized to retrieve relevant audio features for analysis. The controller or processor may utilize time-frequency domain features, e.g., MFCC, SoundNet, or similar neural network based architecture or any combination to extract the relevant features. At step 307, the system may classify the acoustic signals. The system may utilize a classifier to classify the audio event. For such classification, an SVM, random forest, or multiplayer perceptron classifier may be used. The classifiers may classify the audio event to the events of interest, including but not limited to a normal health condition, heart arrhythmia, coronary artery disease, coughing, sneezing, wheezing, shortness of breath, asthma, and other cardiovascular and respiratory disease. Prior to this classification, the classifier is trained utilizing collected data covering all classes of interest. At step 309, the system may utilize time-series aggregation. During the time series aggregation, the health condition detected throughout the entire sensing period may be aggregated. For example, the system may calculate how many times a person showed a case of heart arrhythmia and other symptoms of illness. It may be used to improve the detection as well. For example, the time-series aggregation process may discard sporadic detection incorrectly classified events by utilizing a majority voting. It may also be utilized to provide a summary of the health condition detected from the entire sensing period. At step 311, the system may utilize visualization to output the aggregated information. For example, the information may be output at the display of the car, an app of a smart phone, or a display. If the health condition is critical, it can be shown immediately without conducting the time-series aggregation, such as in step 309.

Figure 4:
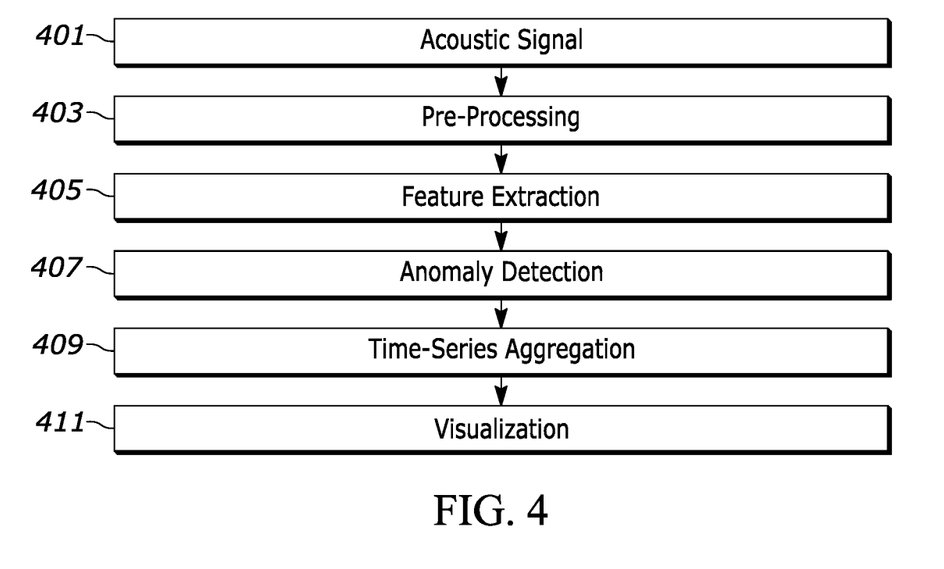
FIG. 4 discloses an alternative flowchart of a computing pipeline for detecting physiological anomaly according to a second embodiment.

FIG. 4 discloses an alternative flowchart of a computing pipeline for detecting physiological anomaly according to a second embodiment. In such an embodiment, the system may not train a classifier for each physiological anomaly. Instead, the system may focus on learning the normal health condition and detect deviation from the normal physiological parameters. The steps for detecting physiological anomalies may use this approach similar to the previous embodiment. However, during the classification phase may not exist. At step 401, the system may collect an acoustic signal. The acoustic signal may come from a one or more acoustic sensors. The acoustic sensors may all be the same type of sensor or may be a mix of various types of sensors. The acoustic sensor may be utilized to collect information related to the user to identify any strange behavior or patterns. At step 403, the system may retrieve the acoustic signals for pre-processing at a circuit. and/or microphones. At step 405, the pre-processed acoustic signal may be fed to a controller or another circuit for feature extraction. The feature extraction may be utilized to retrieve relevant audio features for analysis. The controller or processor may utilize time-frequency domain features, e.g., AfFCC, SoundNet, or similar neural network based architecture or any combination to extract the relevant features. At step 407, the system may determine if any anomalies are detected. The system may utilize an anomaly detector to detect deviations from normal health conditions using the features extracted. If the deviation is beyond a pre-defined threshold, then it may report this as an anomaly. Prior to this, features of normal health condition and anomalous health conditions are fed to a clustering algorithm to tune its parameters to cluster normal health condition from the rest. For clustering algorithm, DBScan, K-means, Agglomerative clustering, spectral clustering, or other clustering algorithm can be utilized. The system can also apply other anomaly detection algorithms on acoustic features. For example, one-class SVM, Gaussian Mixture Model, and auto-encoders may be utilized. At step 409, the system may utilize time-series aggregation. During the time series aggregation, the health condition detected throughout the entire sensing period may be aggregated. For example, the system may calculate how many times a person showed a case of heart arrhythmia and other symptoms of illness. It may be used to improve the detection as well. For example, the time-series aggregation process may discard sporadic detection incorrectly classified events by utilizing a majority voting. It may also be utilized to provide a summary of the health condition detected from the entire sensing period. At step 411, the system may utilize visualization to output the aggregated information. For example, the information may be output at the display of the car, an app of a smart phone, or a display. If the health condition is critical, it can be shown immediately without conducting the time-series aggregation, such as in step 409.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A vehicle system, including:
a vehicle seat, wherein the vehicle seat includes a seat-back portion, a seat-bottom portion, wherein the vehicle seat includes a plurality of acoustic sensors configured to retrieve an acoustic signal associated with a passenger seat; and
a processor in communication with the plurality of acoustic sensors, wherein the processor is programmed to:
identify an anomaly associated with the passenger utilizing the acoustic signal, wherein the anomaly is identified via pre-processing the acoustic signal and extracting one or more features associated with the pre-processed acoustic signal upon the pre-preprocessing and utilizing a classifier to classify one or more features associated with the acoustic signal as either a normal condition or the anomaly, wherein the normal condition and anomaly are associated with cardiovascular features and respiratory features;
output information associated with the normal condition in response to both identifying the normal condition and utilizing a time-series aggregation that utilize time-frequency domain acoustic features from a window of a sensing period, and classifying the window utilizing the classifier and discarding sporadic detection of incorrectly classified events by utilizing majority voting; and
output a notification associated with the anomaly in response to identifying the anomaly.

2. The vehicle system of claim 1, wherein the one or more features are extracted utilizing Mel Frequency Cepstral Coefficients (MFCC), SoundNet convolutional neural network (CNN), time domain features, or frequency domain features.

3. The vehicle system of claim 1, wherein the classifier is trained to identify the anomaly via machine learning.

4. The vehicle system of claim 1, wherein the seat-back portion of the seat includes two acoustic sensors aligned in an array fashion.

5. The vehicle system of claim 1, wherein the seat-back portion of the seat includes three acoustic sensors aligned in an array fashion.

6. The vehicle system of claim 1, wherein the seat-back portion of the seat includes four acoustic sensors aligned in a rectangular array fashion.

7. The vehicle system of claim 1, wherein the seat-back portion of the seat includes the plurality of acoustic sensors aligned in a circular array fashion.

8. A vehicle system, including:
a vehicle seat, wherein the vehicle seat includes a seat-back portion, a seat-bottom portion, wherein the vehicle seat includes a plurality of acoustic sensors configured to retrieve an acoustic signal associated with a passenger seat; and
a processor in communication with at least the plurality of acoustic sensors, wherein the processor is programmed to:
classify the acoustic signal as an anomaly or normal condition, wherein the classifying is accomplished pre-processing the acoustic signal and extracting one or more features associated with the pre-processed acoustic signal in response to the pre-preprocessing and utilizing a classifier to classify one or more features associated with the acoustic signal as the normal condition or the anomaly;
output information associated with the normal condition in response to both identifying the normal condition and utilizing a time-series aggregation that utilize time-frequency domain acoustic features from a window of a sensing period, and classifying the window utilizing the classifier and discarding sporadic detection of incorrectly classified events by utilizing majority voting; and
output a notification associated with the anomaly in response to identifying the anomaly.

9. The vehicle system of claim 8, wherein the one or more features are extracted utilizing Mel Frequency Cepstral Coefficients (MFCC), SoundNet convolutional neural network (CNN), time domain features, or frequency domain features.

10. The vehicle system of claim 8, wherein the classifier is trained to identify the anomaly via machine learning.

11. The vehicle system of claim 8, wherein the plurality of acoustic sensors is a microphone.

12. The vehicle system of claim 8, wherein the seat-back portion of the seat includes the plurality of acoustic sensors aligned in a circular array fashion.

13. The vehicle system of claim 8, wherein the seat-back portion of the seat includes the plurality of acoustic sensors aligned in a rectangular array fashion.

14. A system, including:
a processor in communication with at least one or more acoustic sensors located in a seat, wherein the processor is programmed to:
   identify an anomaly associated with a passenger utilizing the acoustic signal, wherein the anomaly is identified via pre-processing an acoustic signal received from the one or more acoustic sensors and extracting one or more features associated with the pre-processed acoustic signal in response to the pre-preprocessing and utilizing one or more features associated with the acoustic signal as the anomaly;
   output information associated with the normal condition in response to both identifying the normal condition and utilizing a time-series aggregation that utilize time-frequency domain acoustic features from a window of a sensing period, and classifying the window utilizing the classifier and discarding sporadic detection of incorrectly classified events by utilizing majority voting; and
   output a notification associated with the anomaly in response to identifying the anomaly.

15. The system of claim 14, wherein the seat is a non-vehicle seat.

16. The system of claim 14, wherein the processor is further programmed to output information associated with a normal condition in response to both identifying the normal condition and utilizing a time-series aggregation.

17. The system of claim 14, wherein the processor is remote from the seat.

18. The system of claim 14, wherein the seat includes a child-car seat.

* * * * *